United States Patent [19]

Goedecke et al.

[11] 4,250,308

[45] Feb. 10, 1981

[54] PROCESS FOR THE RECOVERY OF SOLID CYANURIC CHLORIDE (A)

[75] Inventors: Ralf Goedecke, Rodenbach; Martin Liebert, Steinbach; Wolfgang Nischk, Wesseling; Uwe Kurandt, Frankfurt am Main; Dieter Mewes, Kleinostheim, all of Fed. Rep. of Germany

[73] Assignee: Deutsche Gold- und Silber-Scheideanstalt vormals Roessler, Hanau, Fed. Rep. of Germany

[21] Appl. No.: 77,920

[22] Filed: Sep. 24, 1979

[30] Foreign Application Priority Data

Oct. 5, 1978 [DE] Fed. Rep. of Germany ....... 2843379

[51] Int. Cl.$^3$ .............................................. C07D 251/28
[52] U.S. Cl. .................................................. 544/190
[58] Field of Search ....................... 544/190; 252/187 C

[56] References Cited

U.S. PATENT DOCUMENTS

| 3,256,070 | 6/1966 | Trickey | 23/294 |
| 3,925,377 | 12/1975 | Geiger et al. | 260/248 |
| 4,038,276 | 7/1977 | Geiger et al. | 260/248 |
| 4,182,871 | 1/1980 | Moller | 544/190 |

FOREIGN PATENT DOCUMENTS

| 1542066 | 3/1970 | Fed. Rep. of Germany . |
| 2332636 | 1/1975 | Fed. Rep. of Germany . |
| 2537673 | 2/1977 | Fed. Rep. of Germany . |
| 2627880 | 12/1977 | Fed. Rep. of Germany . |

OTHER PUBLICATIONS

Ullmann, "Enzyklopadie der Technischen Chemie," 3rd Ed., (1954), vol. 5, pp. 624–625.
Schellenberg, *Chemie, Ing. Tech.*, 38th Year 1966, No. 3, pp. 342–346.

*Primary Examiner*—John M. Ford
*Attorney, Agent, or Firm*—Cushman, Darby & Cushman

[57] ABSTRACT

Solid cyanuric chloride is recovered by a process of spraying liquid cyanuric chloride which preferably is freed from chlorine and cyanogen chloride to the maximum extent possible, the cyanuric chloride is sprayed with the aid of known spraying apparatus into a separation container and solidified by indirect cooling.

12 Claims, 1 Drawing Figure

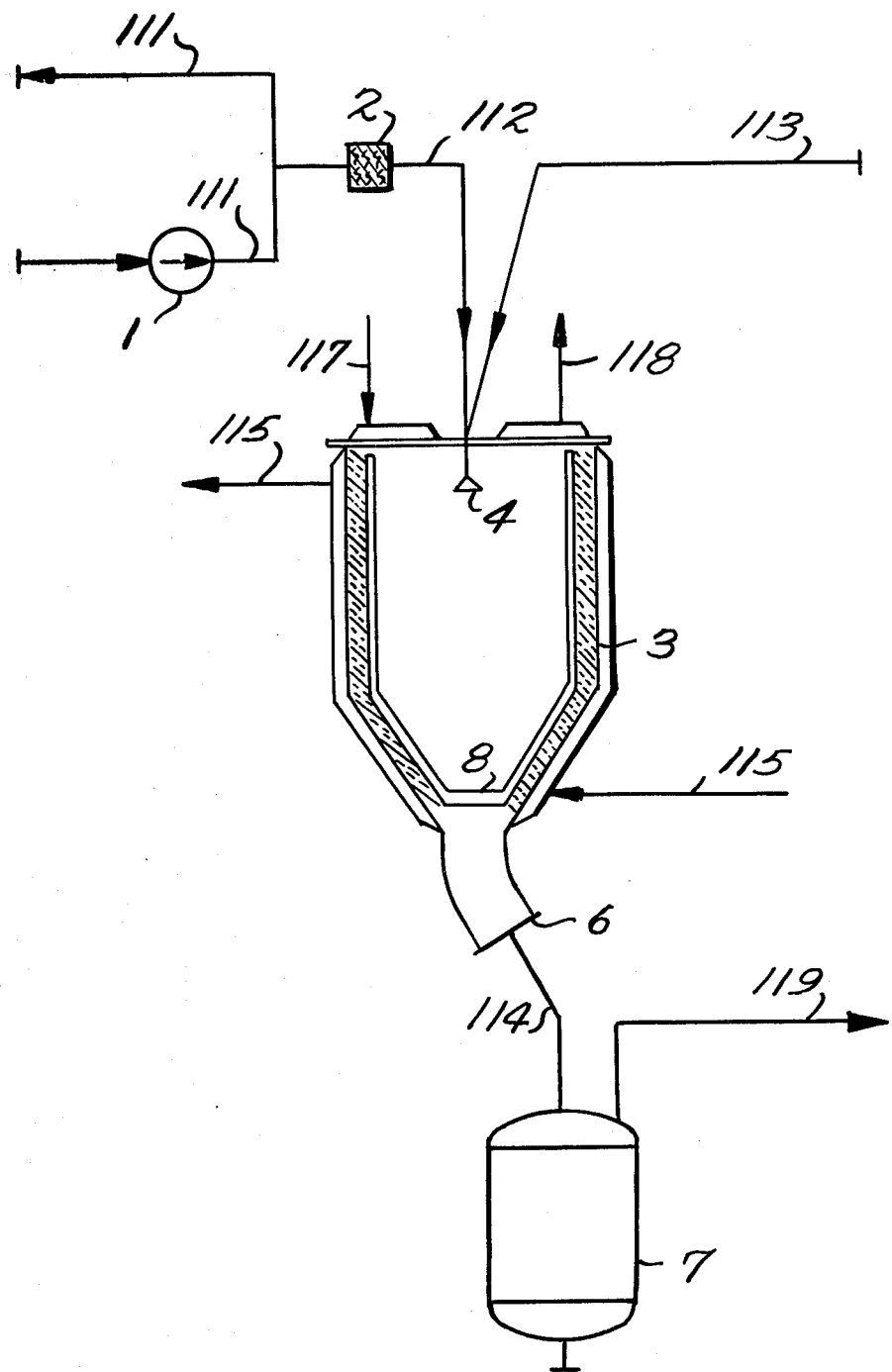

PROCESS FOR THE RECOVERY OF SOLID CYANURIC CHLORIDE (A)

BACKGROUND OF THE INVENTION

Cyanuric chloride which is recovered by trimerization of cyanogen chloride with the help of catalyst, above all activated carbon, as is known is a very interesting intermediate product for various industrial sectors such as the production of dyestuffs and products for the textile industry, as well as for pharmaceuticals, products for agriculture as well as for the synthetic resin, rubber and explosives industries.

As is known after the trimerization cyanuric chloride is obtained in gaseous form together with unreacted cyanogen chloride and chlorine as well as byproducts.

For a long time, it was customary to convert this gaseous reaction mixture directly into solid cyanuric chloride, e.g., by conducting the gaseous mixture into a chamber cooled from the outside (see Ullmann, Enzyklopadie der technischen Chemie, 3rd Edition, 1954, Volume 5, pages 624–625 and 4th Edition, 1975, Volume 9, page 652).

It has also been passed into a ball mill cooled with water according to the process of Trickey U.S. Pat. No. 3,256,070.

Solid cyanuric chloride generally is obtained in powdery form and until now was predominantly further processed in this form.

A disadvantage of the solid cyanuric chloride, however, is that it is frequently not simple to handle.

In the recovery of solid cyanuric chloride by direct desublimation of the reaction gases in separation chambers it was a disadvantage that it was difficult to produce fine-grained products with a narrow grain spectrum.

Thus a part of the cyanuric chloride frequently deposited in the form of coarse crystals on the walls and installations of the desublimation chambers which then had to be mechanically knocked off and had to be reduced to the smaller grain diameter in a subsequent step, entirely apart from the interruption in operating required thereby.

The net result was that residues of chlorine and cyanogen chloride were still enclosed in the final product as a result of which not only caking occurred but also the storage and further processing of the cyanuric chloride was made more difficult.

Furthermore because of corrosive reaction gas constituents chlorine and cyanogen chloride there is also the danger of corrosions in the separatory and discharge aggregates.

Therefore there were endeavors to find other ways for the recovery of cyanuric chloride from the reaction gases.

Thus there are processes known in which the cyanuric chloride contained in the reaction gas is liquified before the solidification and then to convert it into fine-grained, solid form by spraying whereby only ⅓ of the heat of desublimation was drawn off, see Geiger German Patent No. 2,537,673 and related Geiger U.S. Pat. No. 4,038,276.

In this process the heat of melting is drawn off by inert gases brought into the separation container. By the use of the liquid cyanuric chloride chlorine and cyanogen chloride is removed before the solidification.

The precipitated solid cyanuric chloride was fine particled but the use of the inert gas as cooling medium required additional processing steps for discharging the cyanuric chloride from the inert gas.

The purpose of the invention is to provide a process for the recovery of cyanuric chloride in fine-grain (or fine particle) form with the aimed at narrow particle spectrum without large expense for apparatus.

SUMMARY OF THE INVENTION

It has now been found that cyanuric chloride can be recovered in fine grain (fine particle) form with a narrow particle size distribution by spraying liquid cyanuric chloride if liquid cyanuric chloride, which preferably is free from chlorine and cyanogen chlorine is sprayed with the help of a conventional spraying apparatus into a separatory container and is solidified through indirect cooling.

The recovery of liquid cyanuric chloride is known of itself. Preferred are the processes of Geiger German Patent No. 2,332,636 or related Geiger U.S. Pat. No. 3,925,377 or Godecke et al U.S. patent application Ser. No. 88,831 filed on Sept. 25, 1979. The entire disclosure of the Geiger U.S. patent is hereby incorporated by reference and relied upon.

As spraying apparatus there are suited in principle any type of distribution organ, as e.g. rotary plates, unary or binary nozzles.

By changing the number of revolutions in using a rotary plate, by varying the inlet pressure in a unary nozzle and by changing the liquid-gas ratio in the binary nozzle the product quality sought can be produced, which is distinguished by very narrow particle fractions, which is a particular advantage for the further processing of the product.

With binary nozzles as propellant gas for cyanuric chloride there are employed inert gases, such as preferably air or nitrogen.

It is desirable to preheat these gases to the same temperature as the liquid cyanuric chloride; in this case a temperature range between 150° and 185° C. is suitable.

The pressure in the separatory container is not critical for the process, generally it is around atmospheric pressure.

In the spraying of cyanuric chloride nozzles, particularly binary nozzles, have proven advantageous which operate with small amounts of additional propellant gas.

With this the amount of waste gas stream removed from the system is confined to a minimum.

Because of the very small loading of waste gas with cyanuric chloride there can be eliminated a solids separation and the expense of apparatus for a waste gas purification can be held low.

In using the above mentioned binary nozzles in which the two media to be sprayed, preferably the liquid and the gaseous medium, before leaving the nozzle outlet cross section are mixed together homogeneously, the mixture accelerated in the nozzles, and this mixture leaves the nozzle cross section with the speed of sound, the average drop diameter of the sprayed molten cyanuric chloride and therewith the particle size of the solid cyanuric chloride can be regulaed through selection of the ratio of the composition of the liquid and gaseous portion of the mixed media.

As is known the kinetic energy of the liquid, which in turn again depends on the exerted pressure (inlet pressure) and grows with increasing inlet pressure is responsible for the acceleration of the mixture.

Besides it is known that in a moving liquid pressure surges occur which act counter to the direction of flow.

From a fixed velocity of flow upward the pressure surge remains constant and no longer acts against the direction of flow, namely when this velocity is the same as the velocity of sound of the homogeneous mixture of the liquid and gaseous portion.

These types of binary nozzles are known of themselves, e.g. in Meszaros German AS No. 1,542,066, Chawla German OS No. 2,627,880, as well as the general principles in Schellenberg, "Chemie-Ing.-Techn.", 38th year, 1966 No. 3 pages 342–346.

With preselected nozzle geometry and a desired cyanuric chloride composition flow for establishment of a fixed particle spectrum the composition ratio of the mixed media of liquid and gaseous phase belonging thereto are determined by a small scale test.

Particle spectra are preferred in which the particle diameter is up to about 98% below 50$\mu$. Here in using the above mentioned binary nozzles there was ascertained the following value in a small scale experiment.

With an amount of 175 kg of liquid cyanuric chloride per hour there was found a composition ratio of cyanuric chloride to air of about 60:1.

The sprayed cyanuric chloride entered into a separatory container in which the droplets were solidified by crystallization. There can be employed customary separation containers, which preferably are jacketed.

The heat elimination needed for the crystallization process takes place because of the convective heat transfer from the atomized cyanuric chloride via the gas phase present in the separatory container on the cooled container walls.

Through this there are avoided additional amounts of inert gas as cooling media.

The customary cooling media such as, e.g., cooling brines or water serve for cooling the container walls.

Small amounts of solid cyanuric chloride on the cooled container walls, which arise through desublimation from the gas phase saturated with cyanuric chloride present in the container are eliminated by stripping apparatus such as, e.g., scrapers or stirring brooms or even by shaking devices.

In this manner there is avoided a formation of undesired wall deposits. These wall deposits cause both a retarding of the elimination of heat by the cooling agent and also a deterioration of the particle size distribution.

It is especially advantageous, parts of the spraying chamber which cannot be maintained free by mechanical stripping apparatuses to maintain free from crystalline deposits by heating these parts to a temperature of, e.g., 80° to 100° C.

The heating can take place, e.g., with customary heating media such as heat carrier oil or vapor or by electrical energy.

The advance in the art of the process of the invention is first in the fact that liquid cyanuric chloride is solidified without additional assistants as was previously necessary for the direct heat exchange with the sprayed cyanuric chloride. Furthermore, by omitting these assistants simultaneously there is also avoided the total expensive processing steps for the recovery of the residual cyanuric chloride from the assistants.

The process of the invention thus in contrast to the processes of the state of the art is substantially simplified.

Besides through the process of the invention it is possible to substantially increase the throughput compared with a direct desublimation.

With the same heat exchange surface compared to the previous desublimation the throughput is increased to about double or more.

The resulting solid product has particularly good flowability, i.e., the product does not cake, which is particularly advantageous in the filling, storing and further processing.

Additionally, the product is of the known purity of over 99% but practically free from chlorine and cyanogen chloride.

The losses of cyanuric chloride through the waste gas leaving the apparatus are negligibly small; the yield therefore is practically quantitative.

This is correct in increased measure if there are employed binary nozzles in which the two media to be sprayed are homogeneously mixed before leaving the nozzle outlet cross section and they operate with small amounts of gas.

It is possible through the process of the invention to get especially well adjustable particle spectra, preferably with a high fine particle portion.

These particles or grains have a porous structure as the particles recovered by the reaction gases resulting from the trimerization through which there is a larger internal surface.

Through this the product obtained according to the process of the invention is particularly well suited for reactions in which it is important to have a greater reaction velocity and also increased selectivity.

It could not be foreseen that in spite of numerous endeavors of the experts to develop an industrial process for recovery of cyanuric chloride with narrow particle spectra an industrial process so simple to carry out continuously could lead to cyanuric chloride in this yield, purity and particle size distribution.

BRIEF DESCRIPTION OF THE DRAWING

The single FIGURE of the drawings is a schematic illustration of a process for carrying out the process of the invention using a binary nozzle.

Referring more specifically to the drawings the liquid cyanuric chloride is supplied from the ring conduit 111 by means of pump 1 via the filter 2 through the tubular conduit 112 of the separatory chamber or container 3 and atomized by means of the spraying aggregate 4 (here: a binary nozzle). All conduits carrying molten cyanuric chloride and aggregates are heated with a suitable heating medium to temperatures between 150° and 180° C.

Simultaneously, there was supplied to the spraying aggregate 4 compressed air from distributor 5 via the tubular conduit 113 which likewise is heated.

There is located on the separatory container 3 at the end of the conical portion the outlet connection 6 over which the solid cyanuric chloride passes through the tubular conduit 114 into the cyanuric chloride silo 7.

The waste gas laden with small amounts of cyanuric chloride dust is removed by suction from silo 7 via the tubular conduit 119 and supplied to a conventional waste gas washing system (not shown).

The separatory container 3 is equipped with a cooling jacket through which the container wall is cooled via the tubular conduit 115 and 116.

The cover of the separatory container 3 is heated via the tubular conduit 117 and 118.

There is located in the separatory container 3 the stirrer 8 through which stripping devices the fixing of cyanuric chloride on the cooled container walls, in a given case also on the bottom and/or on the cover, is prevented if no conical portion is present.

Unless otherwise indicated all parts and percentages are by weight.

The process can comprise, consist essentially of or consist of the step set forth and the materials employed can comprise, consist essentially of or consist of those set forth.

DESCRIPTION OF THE PREFERRED EMBODIMENT

EXAMPLE 1

There were sprayed into the separatory container 3 (diameter 0.8 meter, height 2.5 meters) from the ring conduit 111 with the help of pump 1 through the filter 2 via the tubular conduit 112 by means of a unary nozzle with a bore diameter 4 of 0.6 mm hourly 7.6 kg of liquid cyanuric chloride having a temperature of 158° C. and a pressure of 6 bar.

The heat withdrawal from the separatory container necessary for the crystallization process was carried out by a cooling water stream with a temperature of about 15° C.

The product was discharged via the conical portion of the separatory container 3 through the outlet opening 6 via the tubular conduit 114 into the product silo 7.

The particle size distribution of the cyanuric chloride obtained was established through sieve analysis as follows:

| | |
|---|---|
| <33μ | 48.2 weight % |
| 33–40μ | 16.4 weight % |
| 40–63μ | 18.80 weight % |
| 63–100μ | 16.2 weight % |
| >100μ | 0.4 weight % |
| >160μ | 0 weight % |

EXAMPLE 2

In contrast with Example 1 the following parameters were changed:

| | |
|---|---|
| Temperature of the cyanuric chloride melt: | 170° C. |
| Bore diameter of the nozzle: | 1.0 mm |
| Cyanuric chloride composition flow: | 34.0 kg/h |

By sieve analysis there was ascertained the following particle size distribution:

| | |
|---|---|
| <33μ | 37.4 weight % |
| 33–40μ | 21.40 weight % |
| 40–63μ | 31.2 weight % |
| 63–100μ | 18.8 weight % |
| >100μ | 1.2 weight % |

EXAMPLE 3

The procedure was the same as in Example 1 with the following changes:

| | |
|---|---|
| Number of unary nozzles: | 5 (with a bore diameter in each case of 1.0 mm) |
| Temperature of the cyanuric chloride melt: | 160° C. |
| Cyanuric chloride composition flow: | 175 kg/h |
| Tower diameter: | 3.5 m |
| Tower height: | 3.5 m |

By sieve analysis there was ascertained the following particle size distribution:

| | |
|---|---|
| <50μ | 61.4 weight % |
| 50–70μ | 14.8 weight % |
| 70–100μ | 9.2 weight % |
| 100–160μ | 10.5 weight % |
| >160μ | 4.1 weight % |

EXAMPLE 4

There were sprayed into the separatory container 3 from the ring conduit 111 with the help of pump 1 through the filter 2 via the tubular conduit 112 and the spray aggregate 4 consisting of a binary nozzle hourly 130 kg of liquid cyanuric chloride having a temperature of 175° C.

Simultaneously there were supplied to the spray aggregate 4 via the tubular conduit 113 1.2 Nm³/h of compressed air at a pressure of 4.0 bar and a temperature of 180° C.

The heat withdrawal from the separatory container (diameter 3.5 meters, height 3.5 meters) necessary for the crystallization process was carried out by a cooling water stream with a temperature of about 15° C.

The product was discharged from the separatory container 3, which in this case did not have a conical portion, through the discharge opening 6 via the tubular conduit 114 into the product silo 7.

The particle size distribution of the cyanuric chloride obtained was established through sieve analysis as follows:

| | |
|---|---|
| <50μ | 95.6 weight % |
| 50–70μ | 2.6 weight % |
| 70–100μ | 1.0 weight % |
| 100–160μ | 0.4 weight % |
| >160μ | 0.4 weight % |

The outgoing air removed from the silo 7 which contained about 1 gram of cyanuric chloride per m³ of gas was washed free of cyanuric chloride in a washer by means of water.

EXAMPLE 5

This example was carried out in the same manner as Example 4 with the following changes:

| | |
|---|---|
| Flow volume of compressed air | 2.5 Nm³/hr |
| Compressed air pressure | 5.5 bar |

The particle size distribution ascertained by sieve analysis was:

| | |
|---|---|
| <50μ | 98 weight % |

-continued

| | |
|---|---|
| 50–70μ | 1.6 weight % |
| 70–100μ | 0.4 weight % |

EXAMPLE 6

This example was carried out in the same manner as Example 4 with the following changes:

| | |
|---|---|
| Flow volume of compressed air | 4.0 Nm³/hr |
| Compressed air pressure | 6.0 bar |

The particle size distribution ascertained by sieve analysis was:

| | |
|---|---|
| <50μ | 99.0 weight % |
| 50–70μ | 1.0 weight % |

EXAMPLE 7

This example was carried out in the same manner as Example 4 with the following changes:

| | |
|---|---|
| Flow volume of compressed air | 0.2 Nm³/h |
| Compressed air pressure | 4 bar |
| Flow of cyanuric chloride composition | 220 kg/h |

The particle size distribution ascertained by sieve analysis was:

| | |
|---|---|
| <50μ | 55.6 weight % |
| 50–70μ | 14.0 weight % |
| 70–100μ | 9.4 weight % |
| 100–160μ | 12.6 weight % |
| >160μ | 8.4 weight % |

EXAMPLE 8

This example was carried out in the same manner as Example 7 with the following changes:

| | |
|---|---|
| Flow volume of compressed air | 0.5 Nm³/hr |
| Compressed air pressure | 5 bar |

The particle size distribution ascertained by sieve analysis was:

| | |
|---|---|
| <50μ | 68.8 weight % |
| 50–70μ | 11.4 weight % |
| 70–100μ | 8.6 weight % |
| 100–160μ | 7.8 weight % |
| >160μ | 3.4 weight % |

EXAMPLE 9

There were sprayed into the separating container 3 (diameter 3.5 meters, height 3.5 meters) from the ring conduit 111 with the help of pump 1 through the filter 2 via the tubular conduit 112 and the spray aggregate 4 consisting of 5 binary nozzles, all of which were simultaneously pressurized, hourly 365 kg of liquid cyanuric chloride having a temperature of 160° C.

Simultaneously there were supplied to the spray aggregate 4 via the tubular conduit 113 12 Nm³/h of compressed air at a pressure of 4.0 bar and a temperature of 180° C.

The heat withdrawal from the separatory container necessary for the crystallization process was carried out through a cooling water stream having a temperature of about 15° C.

The product was discharged from the separatory container 3, which in this case did not have a conical portion, through the discharge opening 6 via the tubular conduit 114 into the product silo 7, the particle size distribution of the cyanuric chloride obtained was established through sieve analysis as follows:

| | |
|---|---|
| <50μ | 94.8 weight % |
| 50–70μ | 3.8 weight % |
| 70–100μ | 1.4 weight % |

The waste air removed from the silo 7 which contained about 1 gram of cyanuric chloride per cubic meter of gas was washed with cyanuric chloride free water in a washer.

EXAMPLE 10

In contrast to Example 9 the cyanuric chloride composition flow was increased to 585 kg/h and the air volume flow reduced to 8.2 Nm³/h.

The following particle size distribution was ascertained by sieve analysis.

| | |
|---|---|
| <50μ | 77.3 weight % |
| 50–70μ | 10.7 weight % |
| 70–100μ | 6.0 weight % |
| 100–160μ | 4.4 weight % |
| >160μ | 1.6 weight % |

EXAMPLE 11

This example was carried out in the same manner as Example 9 with the following changes:

| | |
|---|---|
| Air volume flow: | 6.5 Nm³/h |
| Cyanuric chloride composition flow: | 730 kg/h |

The following particle size distribution was ascertained by sieve analysis.

| | |
|---|---|
| <50μ | 56.4 weight % |
| 50–70μ | 15.6 weight % |
| 70–100μ | 9.2 weight % |
| 100–160μ | 11.2 weight % |
| >160μ | 7.6 weight % |

EXAMPLE 12

In contrast to Example 9 the cyanuric chloride composition flow was increased to 1,000 kg/h and the air volume flow increased to 32.8 Nm³/h.

The particle size distribution was:

| | |
|---|---|
| <50μ | 93.7 weight % |

| | |
|---|---|
| 50–70μ | 4.1 weight % |
| 70–100μ | 2.0 weight % |
| >100μ | 0.2 weight % |

What is claimed is:

1. A process for the recovery of solid cyanuric chloride by spraying liquid cyanuric chloride comprising spraying the cyanuric chloride into a separatory container while indirectly cooling said container sufficiently to solidify the cyanuric chloride.

2. The process of claim 1 wherein the liquid cyanuric chloride that is sprayed into the separatory container is substantially free from chlorine and cyanogen chloride.

3. The process of claim 2 wherein the spraying is carried out with the help of an inert propellant gas.

4. The process of claim 3 wherein the spraying is carried out through a unary nozzle.

5. The process of claim 3 wherein the spraying is carried out through a binary nozzle.

6. The process of claim 5 wherein the liquid cyanuric chloride and the inert propellant gas are homogeneously mixed before leaving the nozzle outlet cross section, and the velocity of the mixture in the nozzle is increased to the extent that the mixture leaves the nozzle outlet cross section with the speed of sound whereby there is controlled the average droplet diameter of the sprayed liquid cyanuric chloride and therewith the particle size of the solid cyanuric chloride formed by the ratio of liquid to gaseous portion of the mixed media.

7. The process of claim 6 comprising keeping the inner surface of the separatory container free from solid cyanuric chloride.

8. The process of claim 7 wherein the surface is maintained free of solids by continuously scraping.

9. The process of claim 7 wherein the surface is maintained free of solids by continuously stirring brooms.

10. The process of claim 1 comprising keeping the inner surface of the separatory container free from solid cyanuric chloride.

11. The process of claim 10 wherein the surface is maintained free of solids by scraping.

12. The process of claim 10 wherein the surface is maintained free of solids by employing stirring brooms.

* * * * *